United States Patent [19]
Franetzki

[11] 3,989,037
[45] Nov. 2, 1976

[54] FLOW MEASURING DEVICE
[75] Inventor: Manfred Franetzki, Erlangen, Germany
[73] Assignee: Siemens Aktiengesellschaft, Munich, Germany
[22] Filed: Mar. 5, 1975
[21] Appl. No.: 555,360

Related U.S. Application Data
[63] Continuation-in-part of Ser. No. 155,190, June 21, 1971, abandoned.

[30] Foreign Application Priority Data
June 23, 1970 Germany............................ 2030775

[52] U.S. Cl................................. 128/2.08; 73/207
[51] Int. Cl.² .......................................... A61B 5/08
[58] Field of Search................. 128/2.08, 2.07, 2 C; 73/207, 210, 205 R, 205 L

[56] References Cited
UNITED STATES PATENTS

| | | | |
|---|---|---|---|
| 1,326,998 | 1/1920 | Wallace | 73/207 |
| 2,125,435 | 8/1938 | Erling | 73/207 X |
| 2,402,585 | 6/1946 | Allison | 73/207 |
| 2,941,401 | 6/1960 | Streeter | 73/210 |
| 2,989,866 | 6/1961 | Widell et al. | 73/207 |
| 3,232,288 | 2/1966 | Krobath | 128/2.08 |
| 3,403,556 | 10/1968 | Koester | 128/2.08 |
| 3,680,378 | 8/1972 | Aurilio et al. | 128/2.08 |

FOREIGN PATENTS OR APPLICATIONS

| | | | |
|---|---|---|---|
| 566,752 | 4/1958 | Belgium | 128/2.08 |
| 880,797 | 1/1943 | France | 128/2.08 |
| 2,030,775 | 12/1971 | Germany | 128/2.08 |

*Primary Examiner*—Robert W. Michell
*Assistant Examiner*—Lee S. Cohen
*Attorney, Agent, or Firm*—Richards & Geier

[57] ABSTRACT

A flow measuring device, particularly a breathing flow receiver for the diagnosis of lung functioning has a flow pipe with a built in diaphragm, from which pressure difference produced by blowing is measured. The device is particularly characterized in that an elastic body, for example, a membrane, is used as the diaphragm, the opening of which changes within the operating range of the pipe by elastic deformation corresponding to flow pressure.

4 Claims, 7 Drawing Figures

FLOW MEASURING DEVICE

This application is a continuation-in-part of the patent application Ser. No. 155,190, filed June 21, 1971, now abandoned, with priority of German application filed June 23, 1970, Ser. No. P2030775. 9, now German Pat. No. 2,030,775, the papers of which are of record in the file of Ser. No. 155,190.

This invention relates to a flow meter, particularly a breathing flow receiver for the diagnosis of lung functioning with a flow pipe having a built in diaphragm from which pressure difference produced during blowing is obtained.

The simplest construction of a flow meter can be provided by the use of a perforated diaphragm. However, pressure measured by such a rigid diaphragm increases substantially with the square of the flow speed. It could be also possible to replace a rigid diagram with an adjustable diaphragm, for example, an iris diaphragm, which could be opened or closed by a suitable drive depending upon the flow speed. Then the characteristic line of the flow meter could be correspondingly changed, particularly made linear.

It is apparent that an operating or regulating circuit for such a variable diaphragm requires substantial construction and most likely will not correspond to requirements since a regulation of the diaphragm opening cannot take place sufficiently quickly and precisely.

An object of the present invention is to improve existing constructions.

Another object is to provide a flow meter wherein by simple means it is possible to provide an extensive adaptation of the characteristic line of the flow pipe with the built in diaphragm to the desired characteristics.

Yet another object is to provide a flow meter of the described type which has a simple structure, is inexpensive and is quite light, so that it can be easily held by the subject, for example, with his teeth.

Other objects of the present invention will become apparent in the course of the following specification.

In the accomplishment of the objectives of the present invention it was found desirable to use as the diaphragm an elastic member, for example, a membrane the opening of which varies within the operating range of the flow pipe by elastic deformation corresponding to the flow pressure.

It is advantageous to build up the membrane from individual elastic lengths fixed to the inner walls of the flow pipe. Furthermore, it is advantageous for the adaptation of the characteristic line that these lengths should have different sizes and/or rigidity. To avoid the work of mounting the lengths it is advantgeous to make them from slits of a foil, for example, from a plastic material. If the slits are correspondingly arranged, lengths having different surfaces are produced and particularly in case of a flow pipe with circular cross-section it is possible to obtain lengths having attaching connections of different widths, so that lengths of different rigidity are produced.

When a flow passes through such a membrane, the first ones to bend will be lengths with the greatest flow receiving surface (for the same connecting width) and the diaphragm opening will be correspondingly increased. This construction makes it possible not only to make linear the characteristic line which is square in a perforated diaphragm, but possibly even to curve it so as to provide a dropping raise of pressure at an increasing gas passage per minute.

Laminar lengths can be replaced by a diaphragm consisting of a rubber-elastic body with openings, which curves by action of flow pressure and thus widens the openings correspondingly.

The invention will appear more clearly from the following detailed description when taken in connection with the accompanying drawings showing by way of example only, preferred embodiments of the inventive idea.

In the drawings:

FIG. 1 shows the characteristic line 1 of the flow pipe with a rigid perforated diaphragm. Furthermore the diagram shows a characteristic line 2 which can be obtained by using a flow pipe with a variable diaphragm opening.

Figure 1:
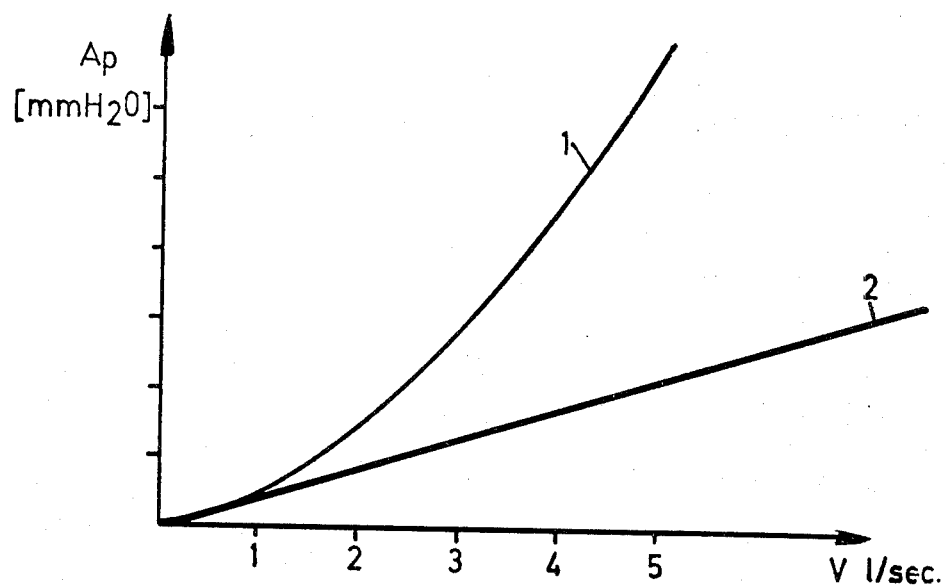
FIG. 1 is a diagram showing the characteristic curve of a flow pipe.
Figure 2:
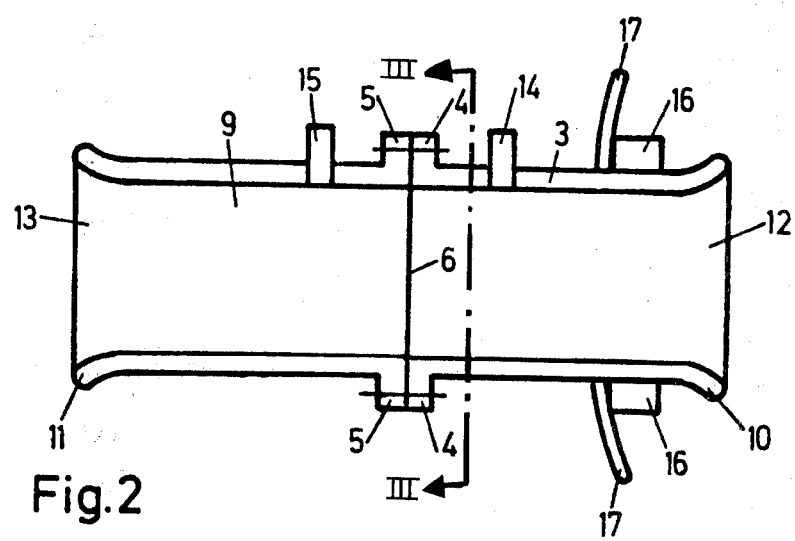
FIG. 2 is a longitudinal section through a flow pipe.
Figure 3:
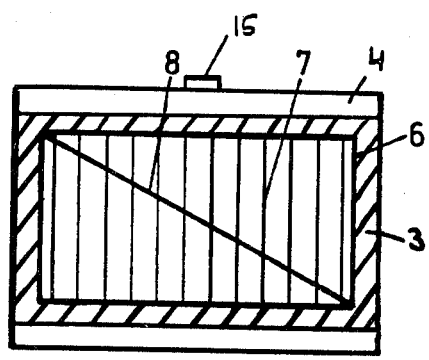
FIG. 3 is a transverse section through the same flow pipe along the line III — III.

The flow pipe 3 shown in FIGS. 2 and 3 carries a membrane 6 between its flanges 4 and 5. The membrane 6 consists of a thin plastic foil having a thickness of 0.05 mm and divided into individual lengths by vertical cuts 7 and a diagonal cut 8 extending across the free pipe cross-section 9. The edges 10 and 11 of the pipe 3 are shaped flow dynamically at the inflow opening 12 as well as at the outflow opening 13, to avoid the formation of whirls. Measured values are obtained from connecting pieces 14 and 15 located on opposite sides of the membrane and are transmitted by flexible pipe lines (not shown) to a suitable differential pressure manometer. A bit piece 16 and a covering lip 17 are provided close to the inlet opening 12, so that the flow pipe can be inserted into the mouth of the subject being examined and be held by his teeth.

As shown in FIG. 2, the membrane 6 can be inserted and fixed between flanges 4 and 5. This provides an easy exchange of the membrane. All parts of the flow pipe can be easily cleaned and disinfected. When using as flow pipe cheap plastic die castings, it is possible to weld the membrane 6 directly between two halves of the flow pipe, so that the breathing flow receivers could be discarded after single use.

Figure 4:
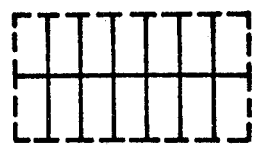
FIG. 4 shows another construction of a membrane.
Figure 5:
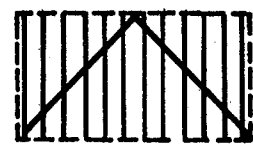
FIG. 5 shows yet another membrane.

FIG. 4 shows a membrane with several vertical cuts and one horizontal cut, while FIG. 5 shows a membrane with several vertical cuts and two transverse cuts. These membranes are to be inserted into rectangular flow pipes.

Figure 6:
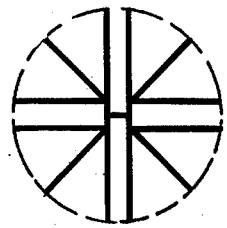
FIG. 6 shows a sectional form of a different membrane.
Figure 7:
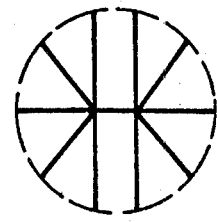
FIG. 7 shows a sectional form of still another membrane.

FIGS. 6 and 7 show cut membranes of the present invention for use with flow pipes having a circular cross-section. It is apparent that by using correspondingly located cut lines it is possible to obtain lengths having a larger surface and a smaller connecting width, as well as lengths having a comparatively smaller surface and a larger connecting width. The smaller the surface the smaller will be the force acting upon the cut lengths and the greater the connecting width the greater will be the release forces, so that cut lengths are produced which will open the diaphragm even when the flow speed is small, as well as such which will become operative only for a high flow speed. These cuts when combined produce a corresponding shape of the characteristic curve which, as already stated, can be not only linearized but even underproportionally curved.

If the cut lines do not extend through the membrane, but if only partial cuts or cutouts are provided and if the membrane is made of rubber-elastic material, then according to the present invention the diaphragm opening can be also changed by curving of the membrane, since such curving produces an opening of the slits or holes.

It is important that when the described membranes or cut lengths are used, the flows in the flow pipe should be uniformly considered in both directions, namely the flow pipe is equally suitable for the breathing-in phase as well as for the breathing-out phase. Due to the adaptation of the diaphragm opening to the flow speed, a very wide operating range is produced, namely with the same cross-section of the flow pipe and the same membrane cuts it is possible to obtain perfectly reproduceable measuring values of, for example, from 0 liter/sec. to 10 liter/sec.

When a pipe of rectangular shape is used the connecting pieces are attached to that side wall of the pipe which has cut membrane pieces with the smallest flow receiving surface.

It is apparent that the described and illustrated embodiments can be varied within the scope of the appended claims.

I claim:

1. A flow meter, particularly a breathing flow receiver for the diagnosis of lung functioning, comprising a flow pipe, having a built in diaphragm, positioned to extend transversely across the interior of said pipe, for producing a difference of pressure between both sides of said diaphragm depending on the strength of flow in said flow pipe, and tubular pneumatical connecting pieces in pneumatical communication with the lumen of said pipe on opposite sides of said diaphragm for obtaining the different pressures on said both opposite sides and supplying them to a differential pressure sensing and indicating means for sensing the difference between said both pressures and indicating the sensed difference of pressure as a direct measure of the strength of flow in said flow pipe, and wherein said diaphragm is an elastic slit membrane consisting of separate cut portions of individual different elastic lengths having different sizes and being attached to inner walls of said pipe, said individual different elastic lengths forming different flow receiving surfaces for the flow pipe.

2. A flow meter in accordance with claim 1, wherein said cut portions consist of foil material having different sizes.

3. A flow meter in accordance with claim 1, wherein said slit membrane consists of a rubber-elastic body with slitlike openings adapted to curve by flow.

4. A flow meter in accordance with claim 1, comprising means carried by said pipe for holding it in the mouth.

* * * * *